United States Patent [19]
Gough

[11] Patent Number: 4,781,798
[45] Date of Patent: Nov. 1, 1988

[54] TRANSPARENT MULTI-OXYGEN SENSOR ARRAY AND METHOD OF USING SAME

[75] Inventor: David A. Gough, Cardiff by the Sea, Calif.

[73] Assignee: The Regents of the University of California, Berkeley, Calif.

[21] Appl. No.: 47,655

[22] Filed: May 8, 1987

Related U.S. Application Data

[63] Continuation of Ser. No. 725,214, Apr. 19, 1985, abandoned.

[51] Int. Cl.[4] .............................................. G01N 27/46
[52] U.S. Cl. ...................... 204/1 T; 204/403; 204/412; 204/415; 128/635; 128/639
[58] Field of Search ............. 204/1 E, 1 P, 1 Y, 403, 204/412, 415; 128/635, 639–641, 643, 644

[56] References Cited
U.S. PATENT DOCUMENTS

| | | | |
|---|---|---|---|
| 3,337,440 | 8/1967 | Nestor | 204/404 |
| 3,871,981 | 3/1975 | Flais et al. | 204/427 |
| 3,985,633 | 10/1976 | Lubbers et al. | 204/415 |
| 4,062,750 | 12/1977 | Butler | 204/415 |
| 4,155,814 | 5/1979 | Tejfalussy et al. | 204/412 |
| 4,252,123 | 2/1981 | Kimmich | 204/415 |
| 4,285,796 | 8/1981 | Stoner et al. | 204/412 |
| 4,522,690 | 6/1985 | Vankatasetty | 204/415 |
| 4,534,356 | 8/1985 | Papadakis | 204/415 |
| 4,536,274 | 8/1985 | Papadakis et al. | 204/415 |
| 4,654,127 | 3/1987 | Baker et al. | 204/412 |

*Primary Examiner*—T. Tung
*Attorney, Agent, or Firm*—Brown, Martin, Haller & Meador

[57] ABSTRACT

A transparent electrochemical oxygen sensor for simultaneously determining oxygen concentration at different locations on a biological surface that is capable of being positioned over the region sought to be measured and includes an array of independently functioning oxygen-sensitive electrodes, a counter electrode, and a reference electrode.

30 Claims, 1 Drawing Sheet

TRANSPARENT MULTI-OXYGEN SENSOR ARRAY AND METHOD OF USING SAME

The invention was made with Government support under grant No. 17421 awarded by National Institutes of Health. The Government has certain rights in this invention.

This is a continuation of application Ser. No. 725,214, filed Apr. 19, 1985, now abandoned.

FIELD OF THE INVENTION

This invention relates to an electrochemical device for determining oxygen concentration on biological surfaces.

BACKGROUND OF THE INVENTION

There exist several electrochemical devices for determining the concentration of various biologically important gases on biological surfaces. Because of the critical role that oxygen plays in physiological events, most of these instruments primarily monitor oxygen, and particularly are employed to monitor oxygen concentrations in patients suffering from disease. The principle on which the instruments operate is that of the common oxygen electrode as described by L. C. Clark, Jr., in *Transactions American Society Artificial Internal Organs* (1956, 2:41). While there exist a number of oxygen sensors suitable for monitoring oxygen at or on such biological surfaces as tissues, organs, blood vessels, etc., none are capable of accurately determining oxygen at different specific locations on the surface. The reasons are two-fold: First, the sensors have not been satisfactorily designed with multiple independent sensing capacity capable of close physical contact with the surface. The latter is required for determining oxygen across nonuniform shaped surfaces. Second, it is difficult to precisely position existing sensors over the diminutive biological structures, particularly superficial blood vessels where it is often desirable to determine the oxygen contour profile across the vessel surface, because it is difficult to visually ascertain where on the surface the electrodes are located.

SUMMARY OF THE INVENTION

This device and method of the invention relate to a transparent array of multiple oxygen sensors capable of determining oxygen concentration on a biological surface and its method of use. The device is constructed using semiconductor fabrication techniques and includes multiple independently operated oxygen-sensing electrodes sufficient in number to measure gradients across the biological surface. The electrodes are situated on a transparent and flexible base, which enables the user to accurately position the sensor over a specific region on the surface under consideration, and, moreover, insures uniform working contact of the sensors with irregularly shaped biological surfaces such as organs, tissues, blood vessels, leaves, etc.

DETAILED DESCRIPTION AND SPECIFIC EMBODIMENTS

Figure 1:
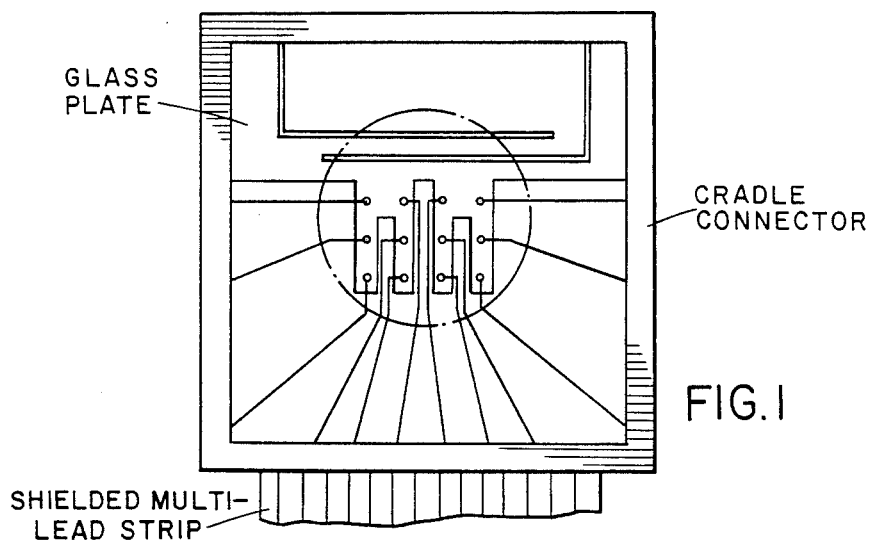
FIG. 1 shows a transparent multi-oxygen sensor with twelve sensing platinum electrodes in a two-dimensional array, a common reference electrode composed of silver-silver chloride and a common platinum counter electrode suitable for testing purposes.
Figure 2:
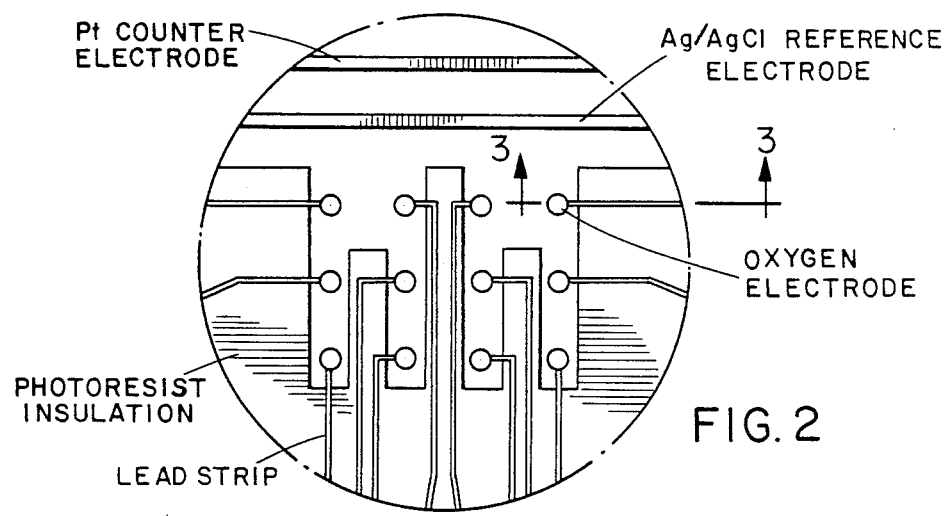
FIG. 2 is an enlarged view of the circled portion in FIG. 1.
Figure 3:
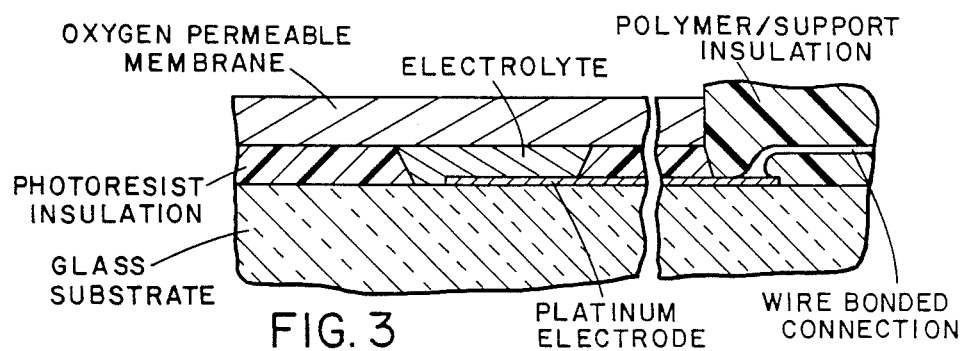
FIG. 3 is a partial sectional view along line 3—3 of FIG. 2.

The transparent multi-oxygen sensor array is fabricated on a suitable transparent substrate that will form the support base on which the electrodes are deposited. The size of the support base is dictated by the area over which an oxygen gradient is sought to be measured, and not by electrochemical considerations. A variety of transparent materials can be used as a support base. Particularly useful are glass or clear plastic, an example of suitable plastic being certain polymers of chlorinated hydrocarbons such as polyvinylidine chloride. Flexible plastic is preferred in those instances where the sensor is utilized to measure oxygen gradients across the surface of irregularly shaped tissues or organs to insure contact of the sensor with the surfaces under consideration.

I. Preparation of the Sensor Base for Electrode Deposition

In order to assure attachment of metals suitable for use as electrodes, it is desirable to clean the surface of the base on which the metals will be deposited. Cleaning of either glass or plastic surfaces can be carried out by various methods, which those skilled in the art will be aware of. A commonly used method is to immerse the base in a sonic bath and subject the base to sonication for an empirically predetermined period of time to remove contaminants from the surface. The base is subsequently rinsed in distilled water.

A second step is required preparatory to depositing metals on glass to insure sufficient bonding of the metals to a glass base. In order to provide a suitable adhesive substratum, it is desirable to etch the surface of the glass base. Several methods are available to etch glass; particularly useful is exposure of glass to a mild acid solution. Illustrative of suitable acids are hydrochloric acid or acetic acid. After etching, the base is rinsed in distilled water and dried under an inert atmosphere such as nitrogen.

II. Deposition of Electrodes

Techniques routinely used to construct integrated circuits are employed to construct the sensor pattern. The techniques are well described by W. S. DeForest in *Photoresist Materials and Processes* (McGraw-Hill, 1975) and numerous other texts, and the nonessential details necessary to construct the sensor are hereby incorporated by reference.

Fabrication of the sensor array is accomplished by depositing, onto one side of the base, under vacuum, noble metals such as platinum or gold routinely used to construct an oxygen sensor. Generally, the multi-oxygen sensor array will have at a minimum three types of electrodes. These are oxygen-sensitive electrodes made of a noble metal, a counter electrode also composed of a noble metal, and a reference silver-silver chloride electrode. It is sometimes convenient to combine the counter and reference electrodes into a single electrode. When the sensor base support is made of glass, it is desirable to deposit an adhesion layer of another metal before depositing the electrode metal, platinum or gold, so as to enhance the binding of the noble metal to the base. Illustrative of a glass-binding metal is chromium. Examples of such deposition techniques are vapor deposition or sputtering. Next, a layer of noble metal about 100 to about 800 angstroms thick is similarly deposited on top of the layer of chromium, and the materials heated between 250° C. to 300° C. for 4 to 5 hours to anneal the layers.

Photolithographic procedures are then employed to establish the electrode pattern. The base is coated using procedures well-known in the art with positive photoresist material on the side containing the metal layers and soft-baked at 90° C. for 25 minutes. 266 Illustrative of positive photoresist material is polyphenolformaldehyde resin, commercially known as novolak resin (e.g., Shipley 1350). The material is coated over the metal layers by spin coating. Next, a lithographic mask suitable for forming the desired number of platinum electrodes in a particular array, of a particular diameter and with sufficient distance between the electrodes is positioned over the base and the plate exposed to ultraviolet light for 25 seconds. The mask is removed and the base is exposed to developer for 40 minutes followed by hard-baking at 120° C. for 30 minutes. The oxygen electrodes are then formed by etching away the platinum and chromium layers. This can be achieved by contacting the base with a dilute mixture of hydrochloric and nitric acids (aqua regia) to etch platinum, followed by a solution of nitric acid and ceric ammonium nitrate to etch chromium.

While there is no one combination of either electrode number, electrode diameter or distance between electrodes that is optimally preferred for adequate performance of the sensor array, it is anticipated that more than a dozen platinum electrodes with diameters of $20\mu$ to $100\mu$ and $40\mu$ to $200\mu$ separation distance will often be employed. It is anticipated that these parameters will be a function of the type of surface and the distance over which an oxygen gradient is sought to be measured.

The procedures used to form the platinum oxygen-sensing measuring electrodes are also employed to form the silver-silver chloride reference electrode. A second deposition of chromium is done using a physical mask to define the area of the intended reference electrode, followed by deposition of silver. Silver is deposited by vapor deposition, sputtering or other suitable techniques. The layers are annealed by heating at 170° C. for 2 hours. In an alternative method the base is again covered with a positive photoresist layer and soft-baked at 90° C. for 25 minutes. Next, a lithographic mask having a negative image of the silver electrode is placed over the base and the base exposed to ultraviolet light for 25 seconds. The mask is removed and the base contacted with developer for 40 seconds followed by hard-baking at 120° C. for 30 minutes. Next, silver is vapor deposited and the photoresist layer is dissolved, leaving the silver electrode pattern. Lastly, the silver is chlorided by electrochemical deposition of chloride from a solution of potassium chloride.

Adequate performance of the sensor requires that the silver reference electrode and counter electrode occupy a particular position on the sensor base. The silver reference electrode must be located between the oxygen sensing electrode array and the counter electrode, preferably closer to the oxygen sensing electrodes. If a combination counter/reference electrode is used, the common electrode may be a silver-silver chloride electrode.

III. Connection of the Sensor to Instrumentation

The platinum sensing electrode, the silver reference electrode and the platinum counter electrode communicate with recording instrumentation through electrical connectors by way of platinum bonding pads, which were formed during the initial deposition of platinum. The bonding pads are situated at the edge of the plate with each electrode being connected to a separate pad, and the pads, in turn, are connected to electrical connectors. The size of the bonding pad can be varied without affecting sensor performance. A satisfactory size is approximately $200\mu$ square. The electrical connectors can be composed of a variety of metals well-known to the those in the art; particularly useful are platinum and gold. The electrical connectors can be bonded to the bonding pads by several techniques, including ultrasonic bonding or applying electrically conductive epoxy to the pads.

IV. Insulation of the Electrodes

The base and all electrodes and connectors contained thereon are coated with photoresist material. This layer acts as an insulator to prevent oxygen from contacting metal surfaces other than those required to detect the presence of oxygen. While photoresist material is a convenient insulator, a variety of other insulating materials can also perform satisfactorily. A thickness of $1\mu$ of insulating layer performs satisfactorily. Application of the photoresist material is achieved by covering the base containing thereon electrodes and electrical connectors with a lithographic mask to define the active electrode areas. The base is then exposed to ultraviolet light for 25 seconds and contacted with developer to expose the areas of the electrodes that are used to detect oxygen. Lastly, the electrical connectors are connected to more substantial lead wires that connect into a multichannel recording instrument.

V. Oxygen-Permeable Membrane

A transparent multi-oxygen sensor array determines oxygen present at the surface of biological surfaces by diffusion of oxygen present through a thin layer of physiological fluids that bathe the surface. Because the sensor electrodes must be in contact with an electrolytic solution to function, and since physiological fluids are high in electrolytes, the sensor can function with the electrodes in direct contact with the fluid. However, in those instances where it is necessary or desirable, to monitor oxygen concentration over a long period of time, it is sometimes seen that prolonged contact of the electrodes with substances present in bodily fluids may poison the electrodes and adversely affect their performance. Thus, to minimize this the surface of the array can be covered with a membrane. For a membrane to be usable in this capacity, it should be permeable to oxygen, impermeable to higher molecular weight substances found in bodily fluids and have relatively good optical properties. At a minimum, it should be partially transparent. Illustrative of materials with these properties is poly(dimethylsiloxane-carbonate) copolymer, which is sold under the trade name of MEM 213 by General Electric. The membrane can be attached to the sensor by a variety of methods well-known to those in the art. Particularly suitable for attachment is cyanoacrylate glue. The membrane must be placed over the array in such a fashion that a small quantity of conductive electrolyte is present between the membrane and the electrodes to make electrical contact.

The following example is provided to illustrate the invention. However, it should be understood that it is not intended to limit the scope of the invention.

EXAMPLE

The transparent multi-oxygen sensor array shown in FIG. 1 was tested for its ability to detect varying levels of oxygen in solution. The sensor was immersed in phosphate buffer, pH 7.3, at 37° C. that had previously been equilibrated with atmospheric oxygen and the resulting currents noted. About 50 nanoamps of current were produced for an oxygen sensor of 150μ diameter; 30 nanoamps for a sensor 75μ diameter; and 15 nanoamps for a sensor of 25μ diameter. On transferring the sensor to a solution containing no oxygen, the sensor displayed a current of 1-2 nanoamps.

I claim:

1. A transparent electrochemical sensor for determining the concentration of a gas at or near biological surfaces comprising:
    a transparent support base;
    a connecting strip comprising a plurality of respective leads attached to an edge of said base;
    a plurality of sensing electrodes, each of 20μ to 100μ diameter, arrayed on a surface of said support base at a spacing of 40μ to 200μ for simultaneously sensing said gas at different regions at or near said biological surface, each of said sensing electrode being independently connected to a respective one of said leads and electrically insulated from all of the others of said sensing electrodes;
    a reference electrode on said surfce and connected to a respective one of said leads;
    a counter electrode on said surface and connected to a respective one of said leads; and
    an electrolyte solution on said surface and in contact with said sensing electrodes, said reference electrode and said counter electrode.

2. A transparent electrochemical sensor as described in claim 1 wherein said gas is oxygen.

3. A transparent electrochemical sensor as described in claim 1 wherein said transparent support base is made of glass.

4. A transparent electrochemical sensor as described in claim 1 wherein said transparent support base is made of a flexible or rigid halogenated hydrocarbon polymer film.

5. A transparent electrochemical sensor as described in claim 1 wherein said sensing electrodes are made of a noble metal.

6. A transparent electrochemical sensor as described in claim 1 wherein said sensing electrodes are situated on said support base in a two-dimensional array.

7. A transparent electrochemical sensor as described in claim 6 wherein said two-dimensional array comprises between eight to thirty-two sensing electrodes.

8. A transparent electrochemical sensor as described in claim 1 wherein said sensing electrodes are coated with insulating material.

9. A transparent electrochemical sensor as described in claim 1 wherein said sensor is covered with a porous oxygen-permeable material which has good optical properties.

10. A transparent electrochemical sensor as described in claim 9 wherein said porous oxygen-permeable material is transparent.

11. A transparent electrochemical sensor as described in claim 10 wherein said porous oxygen-permeable material is selected from the group consisting of polymers of poly(dimethylsiloxane-carbonate), polyethylene or tetrafluoroethylene.

12. A transparent electrochemical sensor as described in claim 9 wherein said porous oxygen-permeable material encloses an electrolytic solution.

13. A transparent electrochemical sensor as described in claim 1 wherein said reference electrode is composed of silver and silver chloride.

14. A transparent electrochemical sensor as described in claim 1 wherein said reference electrode is situated between said sensing electrodes and said counter electrode.

15. A transparent electrochemical sensor as described in claim 1 wherein said counter electrode is composed of a noble metal.

16. A method of meauring the concentration of a gas on biological surfaces comprising:
    providing a transparent electrochemical sensor having a transparent support base, a connecting strip on said base with a plurality of respective leads attached to an edge of said base, a plurality of sensing electrodes each of 20μ to 100μ diameter on a surface of said base at a spacing of 40μ to 200μ, each of said sensing electrodes being independently connected to a respective one of said leads and electrically insulated from all of the others of said sensing electrodes, said electrodes including a reference electrode and a counter electrode, and an electrolyte solution on said base and contacting said electrodes;
    contacting said biological surface with said transparent support base; and
    detecting said gas at different regions of said biological surface contacted by said transparent support base.

17. A method as described in claim 16 wherein said gas is oxygen.

18. A method as described in claim 16 wherein said transparent support base is made of glass.

19. A method as described in claim 16 wherein said transparent support base is made of a flexible or rigid halogenated hydrocarbon polymer film.

20. A method as described in claim 16 wherein said sensing electrodes are made of a noble metal.

21. A method as described in claim 16 wherein said sensing electrodes are situated on said support surface in a two-dimensional array.

22. A method as described in claim 21 wherein said two-dimensional array comprises between eight to thirty-two measuring electrodes.

23. A method as described in claim 16 wherein said sensing electrodes are coated with insulating material.

24. A method as described in claim 16 wherein said transparent electrochemical sensor is covered with porous oxygen-permeable material which has good optical properties.

25. A method as described in claim 24 wherein said porous oxygen-permeable material is transparent.

26. A method as described in claim 25 wherein said porous oxygen-permeable material is selected from the group consisting of polymers of poly (dimethylsiloxane-carbonate), polyethylene or tetrafluoroethylene.

27. A method as described in claim 16 wherein said porous oxygen-permeable material encloses an electrolytic solution.

28. A method as described in claim 18 wherein said reference electrode is composed of silver and silver chloride.

29. A method as described in claim 16 wherein said reference electrode is situated between said sensing electrodes and said counter electrode.

30. A method as described in claim 16 wherein said counter electrode is composed of a noble metal.

* * * * *